US006214796B1

(12) United States Patent
Finklestein

(10) Patent No.: US 6,214,796 B1
(45) Date of Patent: *Apr. 10, 2001

(54) ADMINISTRATION OF POLYPEPTIDE GROWTH FACTORS FOLLOWING CENTRAL NERVOUS SYSTEM ISCHEMIA OR TRAUMA

(75) Inventor: Seth P. Finklestein, Needham, MA (US)

(73) Assignee: The General Hospital Corporation, Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/822,455

(22) Filed: Mar. 21, 1997

Related U.S. Application Data

(63) Continuation-in-part of application No. 08/620,444, filed on Mar. 22, 1996.

(51) Int. Cl.$^7$ .................................................. A61K 38/00
(52) U.S. Cl. ............................................. 514/12; 530/399
(58) Field of Search ............................... 514/12; 530/399

(56) References Cited

U.S. PATENT DOCUMENTS

| | | | |
|---|---|---|---|
| 4,296,100 | 10/1981 | Franco | 424/565 |
| 4,378,347 | * 3/1983 | Franco | 424/108 |
| 4,994,559 | 2/1991 | Moscatelli et al. | 530/399 |
| 5,011,914 | 4/1991 | Collins et al. | 530/399 |
| 5,057,494 | 10/1991 | Sheffield | 514/12 |

FOREIGN PATENT DOCUMENTS

| | | |
|---|---|---|
| 501445 A1 | 9/1991 | (EP) . |
| 9308828 | * 5/1993 | (WO) . |
| 9309802 | * 5/1993 | (WO) . |
| WO 93/09802 | 5/1993 | (WO) . |
| 9412201 | * 9/1994 | (WO) . |

OTHER PUBLICATIONS

Fisher et al., *J. Cereb. Blood Flow Metab.* 15(6), 953–9, 1995.*

Lyons et al., *Brain Res.*, 558(2), 315–20, 1991.*

Masuda, T., *Kagoshima Daigaku Igaku Zasshi*, 46(2), 67–76, 1994.*

Yamada et al., *J. Cereb. Blood Flow Metab.*, 11(3), 472–8, 1991.*

Burgess et al., "The Heparin–Binding (Fibroblast) Growth Factor Family of Proteins", *Annual Rev. Biochem.*, 58:575–606 (1989).

Fisher et al., "Delayed Treatment with Intraveneous Basic Fibroblast Growth Factor Reduces Infarct . . . . ", *Journal of Cerebral Blood Flow and Metabolism*, 15:953–959 (1995).

Florkiewicz et al., "Human basic fibroblast growth factor gene encodes four polypeptides: Three initiate translation from non–AUG codons", *Proc. Natl. Acad. Sci.*, 86:3978–3981 (1989).

Gotti et al., "The pharmacotherapy of focal cortical ischaemia in the mouse", *Brain Research*, 522:290–307 (1990).

Jiang et al., "Delayed intravenous administration of basic fibroblast growth factor (bFGF) reduces . . . ", *Journal of the Neurological Sciences*, 139:173–179 (1996).

Kawamata et al., "Intracisternal Basic Fibroblast Growth Factor (bFGF), Enhances Behavioral . . . . ", *Journal of Cerebral Blood Flow and Metabolism*, 16:542–547 (1996).

Morrison et al., "Basic fibroblast growth factor supports the survival of cerebral cortical neurons in primary culture", *Proc. Natl. Acad. Sci.*, 83:7537–7541 (1986).

Rosenberg et al., "Excitotoxic Neuronal Disease: Future Therapies for Epilepsy, Stroke . . . , " *Continum, Lifelong learning in neurology*, 2:92–112 (1996).

Skene et al., "Axonal Growth–Associated Proteins", *Am. Rev. Neurosci.*, 12:127–56 (1989).

Tanaka et al., "Basic Fibroblast Growth Factor Increases Regional Cerebral Blood Flow and Reduces . . . ", *Stroke*, 26(11) (1995).

Thomas, "Fibroblast growth factors", *The FASEB Journal*, 1:434–440 (1987).

Yamada et al., "Basic Fibroblast Growth Factor Prevents Thalamic Degeneration After Cortical . . . . ", *Journal of Cerebral Blood Flow and Metabolism*, 11:472–478 (1991).

Finklestein et al., Stroke 21–III–124, 1990.

* cited by examiner

*Primary Examiner*—Dwayne C. Jones
*Assistant Examiner*—C. Delacroix-Muirhead
(74) *Attorney, Agent, or Firm*—Fish & Richardson P.C.

(57) ABSTRACT

The present invention relates to the treatment of central nervous system injuries by intracisternal or intravenous administration of polypeptide growth factors, such as basic fibroblast growth factor. This method provides significant benefits because administration can occur a substantial amount of time following an injury.

26 Claims, 15 Drawing Sheets

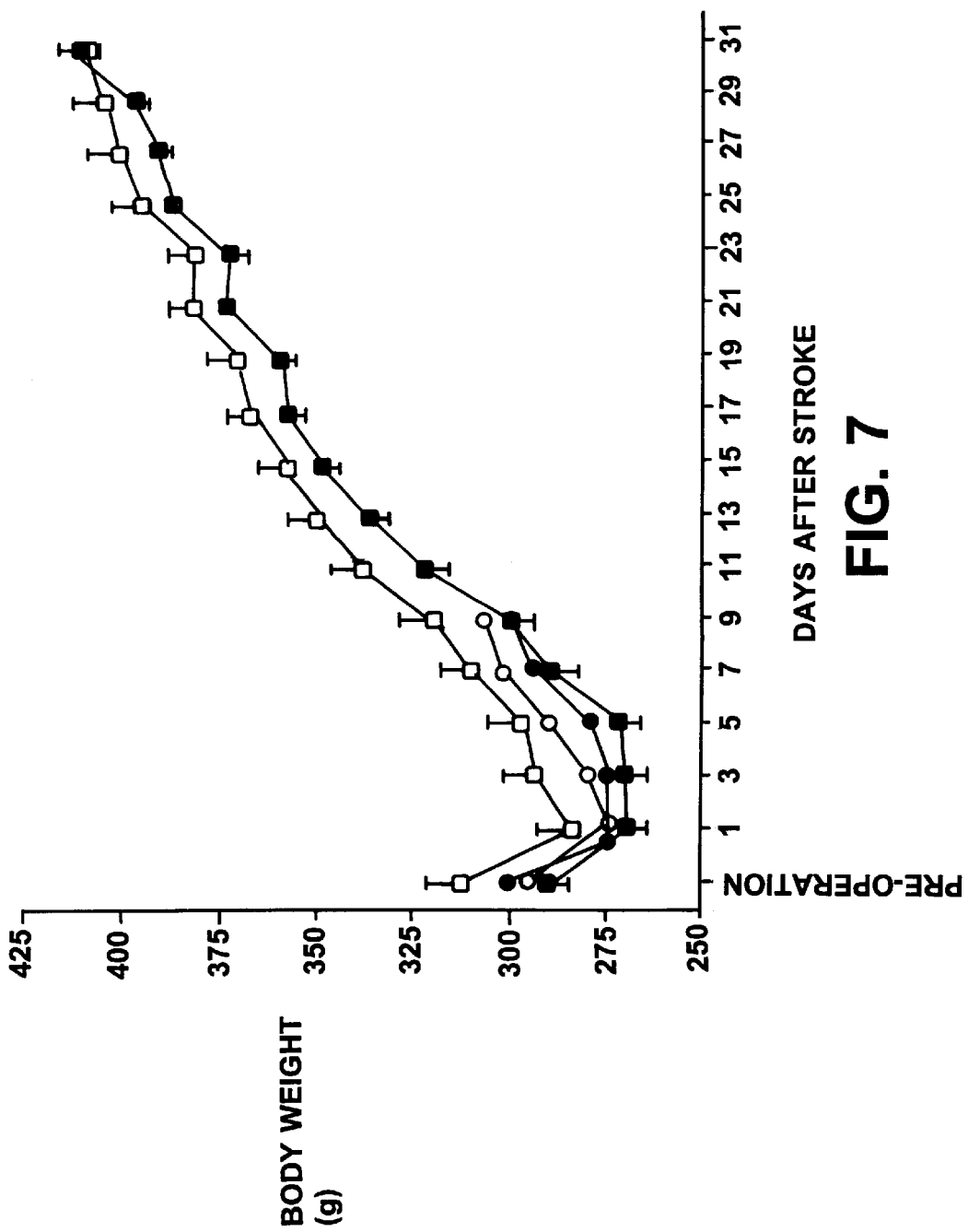

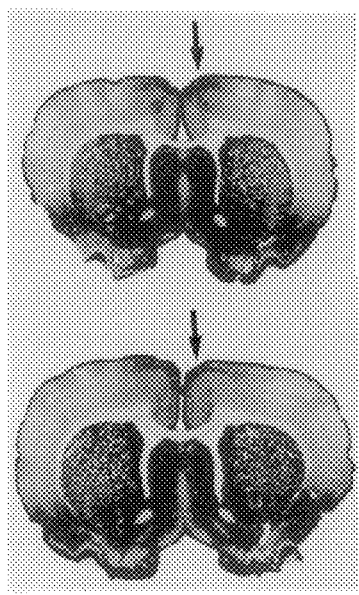
FIG. 9A
FIG. 9C
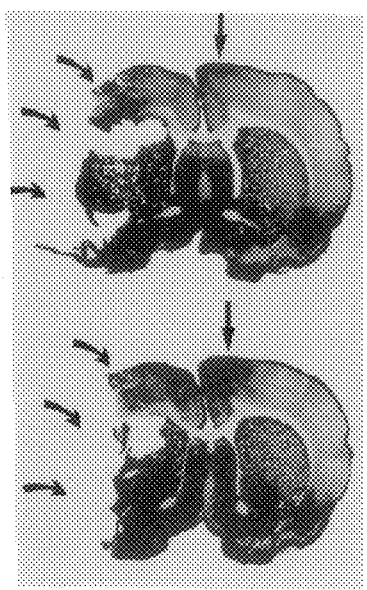
FIG. 9B
FIG. 9D
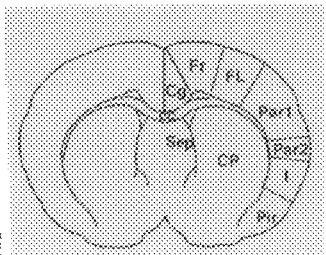
FIG. 9E

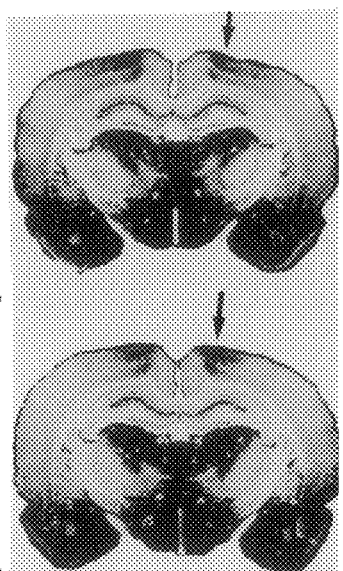
FIG. 10A
FIG. 10C
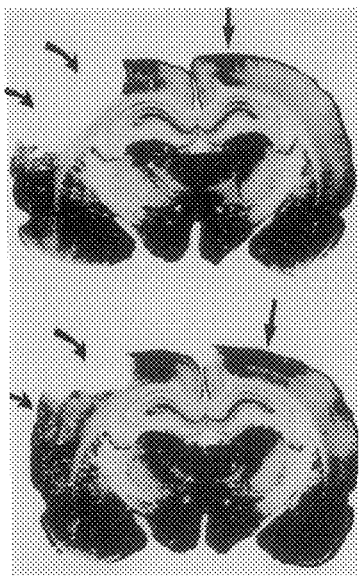
FIG. 10B
FIG. 10D
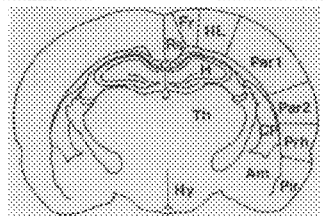
FIG. 10E

ADMINISTRATION OF POLYPEPTIDE GROWTH FACTORS FOLLOWING CENTRAL NERVOUS SYSTEM ISCHEMIA OR TRAUMA

This application is a continuation-in-part of U.S. Ser. No. 08/620,444, filed Mar. 22,1996.

The work described herein was supported in part by a grant from the National Institutes of Health (PO1 NS 10828). The government therefore has certain rights in the invention.

The field of the invention is the treatment of ischemic injury of the central nervous system.

BACKGROUND OF THE INVENTION

Neurotrophic factors are polypeptides that are required for the development of the nervous system. The first neurotrophic factor discovered, nerve growth factor (NGF), is now known to be a part of a large family of growth factors, which also includes brain-derived neurotrophic factor (BDNF) and the neurotrophins (NT3 and NT4/NT5). Fibroblast growth factors (FGFs) constitute another large family of polypeptide growth factors that induce mitogenic, chemotactic, and angiogenic activity in a wide variety of cells, including neurons (Thomas, *FASEB J.* 1:434–440, 1987; Burgess et al., *Ann. Rev. Biochem.* 58:575–606, 1989; Moscatelli et al., U.S. Pat. No. 4,994,559). While the role of polypeptide growth factors in the developing animal has become increasingly evident, their role in the mature animal, particularly in the nervous system, is much less clear.

Injury or death of neurons in a mature animal produces motor and/or cognitive deficits that are often permanent. Patients who suffer a "stroke," or any other form of cerebral ischemic episode, usually recover partially, but often remain mildly to severely debilitated. Currently, aside from physical therapy, there is no treatment that reliably improves the prognosis of a patient who has suffered a cerebral ischemic episode.

SUMMARY OF THE INVENTION

We have discovered that administration of a polypeptide growth factor provides significant benefits following a cerebral ischemic episode, even when administration occurs a significant amount of time following that episode. Furthermore, functional recovery occurs without a reduction in the size of the infarct (i.e., the necrotic tissue that is produced by ischemia).

Accordingly, the invention features a method for treating a patient who has suffered an injury to the central nervous system, such as an ischemic episode or a traumatic injury, by administering to the patient a polypeptide growth factor, wherein administration occurs more than six hours after the onset of the injury; administration can beneficially occur even later, i.e., twelve, twenty-four, forty-eight, or more hours following the ischemic episode.

The polypeptide growth factor administered may be: a member of the fibroblast growth factor (FGF) family, such as basic FGF (bFGF), acidic FGF (aFGF), the hst/Kfgf gene product, FGF-5, or int-2; a member of the neurotrophin family, such as nerve growth factor (NGF), brain-derived neurotrophic factor (BDNF), neurotrophin 3 (NT3), or neurotrophin 4/5 (NT4/5); an insulin-like growth factor (IGF), such as IGF-1, or IGF-2; ciliary neurotrophic growth factor (CNTF); leukemia inhibitory factor (LIF); oncostatin M; or an interleukin.

Also included in the invention are "functional polypeptide growth factors," which possess one or more of the biological functions or activities of the polypeptide growth factors described herein. These functions or activities are described in detail below and concern, primarily, enhancement of recovery following an ischemic event within the central nervous system. Accordingly, alternate molecular forms of polypeptide growth factors are within the scope of the invention. For example, forms of bFGF have been observed with molecular weights of 17.8, 22.5, 23.1, and 24.2 kDa. The higher molecular weight forms being colinear N-terminal extensions of the 17.8 kDa bFGF (Florkiewicz et al., *Proc. Natl. Acad. Sci. USA* 86:3978–3981, 1989).

Alternatively, polypeptide growth factors useful in the invention can consist of active fragments of the factors. By "active fragment," as used herein in reference to polypeptide growth factors, is meant any portion of a polypeptide that is capable of invoking the same activity as the full-length polypeptide. The active fragment will produce at least 40%, preferably at least 50%, more preferably at least 70%, and most preferably at least 90% (including up to 100%) of the activity of the full-length polypeptide. The activity of any given fragment can be readily determined in any number of ways. For example, a fragment of bFGF that, when administered according to the methods of the invention described herein, is shown to produce performance in functional tests that is comparable to the performance that is produced by administration of the full-length bFGF polypeptide, would be an "active fragment" of bFGF. It is well within the abilities of skilled artisans to determine whether a polypeptide growth factor, regardless of size, retains the functional activity of a full length, wild type polypeptide growth factor.

As used herein, both "protein" and "polypeptide" mean any chain of amino acid residues, regardless of length or post-translational modification (e.g., glycosylation or phosphorylation). The polypeptide growth factors useful in the invention are referred to as "substantially pure," meaning that a composition containing the polypeptide is at least 60% by weight (dry weight) the polypeptide of interest, e.g., a bFGF polypeptide. Preferably, the polypeptide composition is at least 75%, more preferably at least 90%, and most preferably at least 99%, by weight, the polypeptide of interest. Purity can be measured by any appropriate standard method, e.g., column chromatography, polyacrylamide gel electrophoresis, or HPLC analysis.

Furthermore, the nomenclature in the field of polypeptide growth factors is complex, primarily because many factors have been isolated independently by different groups of researchers and, historically, named for the type of tissue that was used as an assay in the process of purifying the factor. Basic FGF has been referred to in scientific publications by at least 23 different names. These include leukemic growth factor, macrophage growth factor, embryonic kidney-derived angiogenesis factor 2, prostatic growth factor, astroglial growth factor 2, endothelial growth factor, tumor angiogenesis factor, hepatoma growth factor, chondrosarcoma growth factor, cartilage-derived growth factor 1, eye-derived growth factor 1, heparin-binding growth factors class II, myogenic growth factor, human placenta purified factor, uterine-derived growth factor, embryonic carcinoma-derived growth factor, human pituitary growth factor, pituitary-derived chondrocyte growth factor, adipocyte growth factor, prostatic osteoblastic factor, and mammary tumor-derived growth factor. Thus, any factor referred to by one of the aforementioned names is considered within the scope of the invention.

The polypeptide growth factors useful in the invention can be naturally occurring, synthetic, or recombinant molecules consisting of a hybrid or chimeric polypeptide with one portion, for example, being bFGF, and a second portion being a distinct polypeptide. These factors can be purified from a biological sample, chemically synthesized, or produced recombinantly by standard techniques (see e.g., Ausubel et al., *Current Protocols in Molecular Biology*, New York, John Wiley and Sons, 1993; Pouwels et al., *Cloning Vectors: A Laboratory Manual*, 1985, Supp. 1987).

The treatment regimen according to the invention is carried out, in terms of administration mode, timing of the administration, and dosage, so that the functional recovery of the patient from the adverse consequences of the central nervous system injury is improved; i.e., the patient's motor skills (e.g., posture, balance, grasp, or gait), cognitive skills, speech, and/or sensory perception (including visual ability, taste, olfaction, and proprioception) improve as a result of polypeptide growth factor administration according to the invention.

Administration of polypeptide growth factors according to the invention can be carried out by any known route of administration, including intravenously, orally, or intracerebrally (e.g., intraventricularly, intrathecally, or intracisternally); intracisternal administration can be carried out, e.g., using 0.1 to 100 $\mu$g/kg/injection and administering a single injection or a series of injections. For example, intracisternal administration can consist of a single injection given, for example, 24 hours after an injury, a pair of injections, given, for example, 24 and 48 hours after an injury, or, if necessary, a series of injections of, for example, 3.0 $\mu$g/kg/injection, given biweekly (for example, every 3–4 days) in a treatment regimen that occurs twenty-four hours or longer following the ischemic episode. The treatment regimen may last a number of weeks. Alternatively, intracisternal administration can consist of a series of injections, at 1.5 $\mu$g/kg/injection, given once, twice, or, for example, biweekly in a treatment regimen that occurs twenty-four hours or longer following the ischemic episode.

Alternatively, the polypeptide growth factors can be administered intravenously. Typically, the dosage for intravenous administration will be greater than that for intracisternal administration, e.g., 10 to 1,000 $\mu$g/kg of a polypeptide growth factor may be administered. Preferably, the polypeptide growth factors are administered intravenously at concentrations ranging from 1–100 $\mu$g/kg/hour. Treatment regimes are discussed in detail below.

The invention can be used to treat the adverse consequences of central nervous system injuries that result from any of a variety of conditions. Thrombus, embolus, and systemic hypotension are among the most common causes of cerebral ischemic episodes. Other injuries may be caused by hypertension, hypertensive cerebral vascular disease, rupture of an aneurysm, an angioma, blood dyscrasias, cardiac failure, cardic arrest, cardiogenic shock, septic shock, head trauma, spinal cord trauma, seizure, bleeding from a tumor, or other blood loss.

Where the ischemia is associated with a stroke, it can be either global or focal ischemia, as defined below. It is believed that the administration of polypeptide growth factors according to the invention is effective, even though administration occurs a significant amount of time following the injury, at least in part because these peptides stimulate the growth of new processes from neurons. In addition, polypeptide growth factors may protect against retrograde neuronal death, i.e., death of the neurons that formed synapses with those that died in the area of the infarct.

By "ischemic episode" is meant any circumstance that results in a deficient supply of blood to a tissue. Cerebral ischemic episodes result from a deficiency in the blood supply to the brain. The spinal cord, which is also a part of the central nervous system, is equally susceptible to ischemia resulting from diminished blood flow. An ischemic episode may be caused by a constriction or obstruction of a blood vessel, as occurs in the case of a thrombus or embolus. Alternatively, the ischemic episode can result from any form of compromised cardiac function, including cardiac arrest, as described above. It is expected that the invention will also be useful for treating injuries to the central nervous system that are caused by mechanical forces, such as a blow to the head or spine. Trauma can involve a tissue insult such as an abrasion, incision, contusion, puncture, compression, etc., such as can arise from traumatic contact of a foreign object with any locus of or appurtenant to the head, neck, or vertebral column. Other forms of traumatic injury can arise from constriction or compression of CNS tissue by an inappropriate accumulation of fluid (for example, a blockade or dysfunction of normal cerebrospinal fluid or vitreous humor fluid production, turnover, or volume regulation, or a subdural or intracranial hematoma or edema). Similarly, traumatic constriction or compression can arise from the presence of a mass of abnormal tissue, such as a metastatic or primary tumor.

By "focal ischemia," as used herein in reference to the central nervous system, is meant the condition that results from the blockage of a single artery that supplies blood to the brain or spinal cord, resulting in the death of all cellular elements (pan-necrosis) in the territory supplied by that artery.

By "global ischemia," as used herein in reference to the central nervous system, is meant the condition that results from a general diminution of blood flow to the entire brain, forebrain, or spinal cord, which causes the death of neurons in selectively vulnerable regions throughout these tissues. The pathology in each of these cases is quite different, as are the clinical correlates. Models of focal ischemia apply to patients with focal cerebral infarction, while models of global ischemia are analogous to cardiac arrest, and other causes of systemic hypotension.

The method of the invention has several advantages. First, polypeptide growth factors can be administered hours, days, weeks, or even months following an injury to the central nervous system. This is advantageous because there is no way to anticipate when such an injury will occur. All of the events that cause ischemia or trauma, as discussed above, are unpredictable. Second, the therapeutic regimen improves functional performance without adverse side effects.

All publications, patents, patent applications, and other references cited herein are incorporated by reference in their entirety.

The preferred methods, materials, and examples that will now be described are illustrative only and are not intended to be limiting; materials and methods similar or equivalent to those described herein can be used in the practice or testing of the invention. Other features and advantages of the invention will be apparent from the following detailed description, and from the claims.

BRIEF DESCRIPTION OF THE DRAWINGS

Note that in FIGS. 2A–2B and 3A–3B, the scores representing performance of rats treated with a total of 8 $\mu$g of bFGF are depicted along the y-axis with lower scores, representing better performance, nearest the intersection with the X-axis. In contrast, in FIGS. 5A–5B and 6A–6B, the scores representing performance of rats treated with a total of 4 µg of bFGF are depicted along the y-axis with lower scores, representing better performance, furthest from the intersection with the X-axis. The change from the former to the latter presentation was made so that improvement would appear as an upward trend, rather than a downward trend.

n.s.=non-significant.

FIG. 7 is a graph demonstrating that there was no difference between the body weight of animals that received low dose bFGF intracisternally (total bFGF delivered=4 µg/animal; N=8 animals; closed squares), animals that received vehicle intracisternally (N=6; open squares; Data are means±SEM. ANOVA: treatment: $F(1)=3.02$, $p=$n.s.), animals that received bFGF intravenously (closed circles), and animals that received vehicle intravenously (open circles).

FIGS. 9A–9E are a series of photographs from an image analyzer (FIGS. 9A–9D) and a schematic drawing (FIG. 9E) of histological sections of rat brain (anterior to bregma) stained for GAP-43 immunoreactivity following surgical induction of stroke and intracisternal bFGF treatment. Anterior sections were collected from a sham-operated/vehicle-treated animal (FIG. 9A), a stroke-induced/vehicle-treated animal (FIG. 9B), a sham-operated/bFGF-treated animal (FIG. 9C), and a stroke-induced/bFGF-treated animal (FIG. 9D). The darker regions represent regions of GAP-43 immunoreactivity where the optical density was 1.5 times or greater compared to that in the corpus callosum in each slice. Curved arrows point to cerebral infarcts. Various brain regions are shown in the schematic diagram (FIG. 9E): Cg=cingulate cortex; FR 1,2=frontal cortex, areas 1 and 2; FL=forelimb are; Par 1,2=parietal cortex, areas 1 and 2; I=insular cortex; Pir=piriform cortex; CC=corpus callosum; Sep=septal nucleus; CP=caudoputamen.

FIGS. 10A–10E are a series of photographs from an image analyzer (FIGS. 10A–10D) and a schematic drawing (FIG. 10E) of histological sections of rat brain (posterior to bregma) stained for GAP-43 immunoreactivity following surgical induction of stroke and intracisternal bFGF treatment. Posterior sections were collected from a sham-operated/vehicle-treated animal (FIG. 10A), a stroke-induced/vehicle-treated animal (FIG. 10B), a sham-operated/bFGF-treated animal (FIG. 10C), and a stroke-induced/bFGF-treated animal (FIG. 10D). The darker regions represent regions of GAP-43 immunoreactivity where the optical density was 1.5 times or greater compared to that in the corpus callosum in each slice. Curved arrows point to cerebral infarcts (in FIG. 10B all necrotic tissue has fallen off the slide; in FIG. 10D some infarcted tissue remains (lower curved arrow), but is necrotic as determined by hemotoxylin and eosin staining of adjacent sections. Various brain regions are shown in the schematic diagram (FIG. 10E): Rs=retrosplenial cortex; FR 1,2=frontal cortex, areas 1 and 2; HL=hindlimb area; Par1,2=parietal cortex, areas 1 and 2; Prh=perirhinal cortex; Pir=piriform cortex; Am=amygdala; CP=caudoputamen; H=hippocampus; Hy=hypothalamus.

DETAILED DESCRIPTION

Figure 1A:
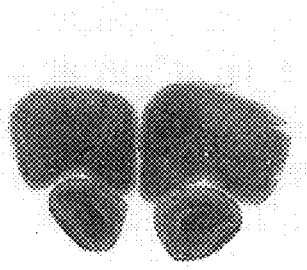
FIGS. 1A–1F are a series of photographs of brain sections stained with hemotoxylin and eosin. A representative cerebral infarct, produced following proximal middle cerebral artery (MCA) occlusion, is shown. Coronal sections are +4.7 (FIG. 1A), +2.7 (FIG. 1B), +0.7 (FIG. 1C), −1.3 (FIG. 1D), −3.3 (FIG. 1E), and −5.3 (FIG. 1F) compared to bregma.
Figure 1B:
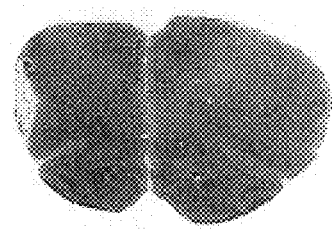
Figure 1C:
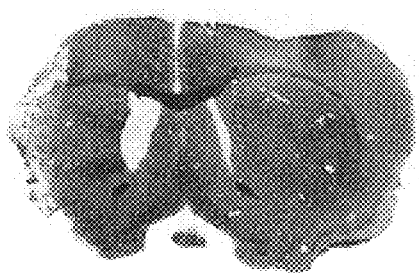
Figure 1D:
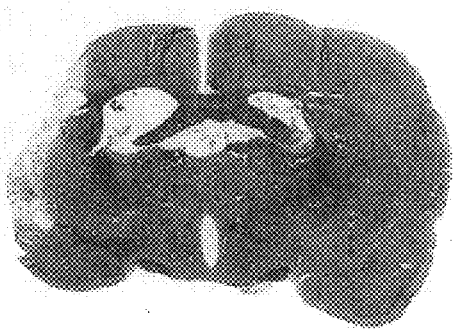
Figure 1E:
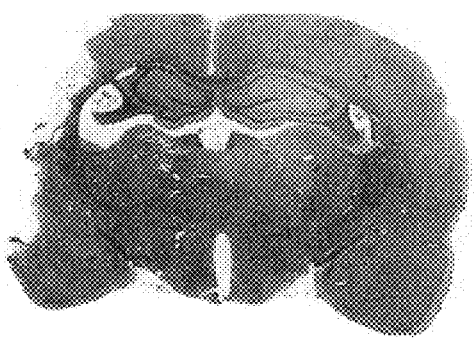
Figure 1F:
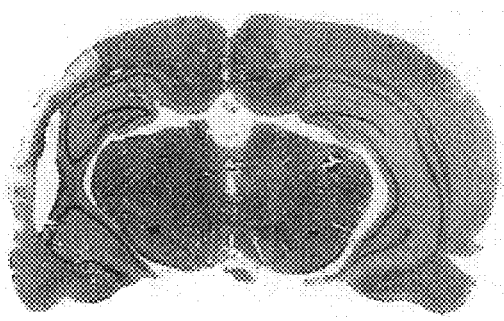
Figure 2A:
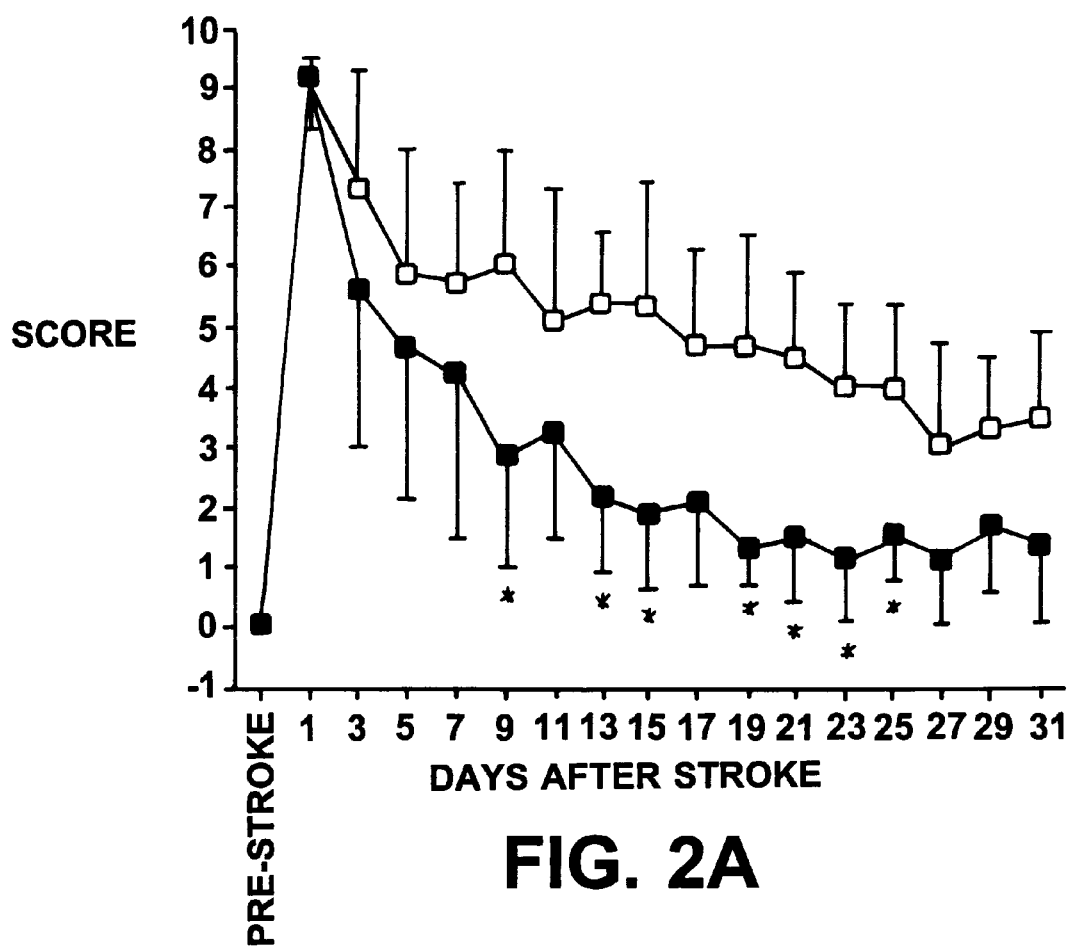
FIGS. 2A–2B are a pair of graphs depicting forelimb placing (2A) and hindlimb placing (2B) scores of affected (left) limbs of bFGF-treated animals (3 µg/kg/injection; total bFGF delivered=8 µg/animal; N=9 animals; closed squares) and vehicle-treated animals (N=8, open squares). Data are means±SD. ANOVA (forelimb placing): treatment: $F(1)=17.7$, $p=0.0008$. ANOVA (hindlimb placing): treatment: $F(1)=26.0$, $p=0.0001$. *=values in bFGF-treated animals different from corresponding values in vehicle-treated animals by two-tailed unpaired t-tests with Bonferroni correction ($p<0.05$).
Figure 2B:
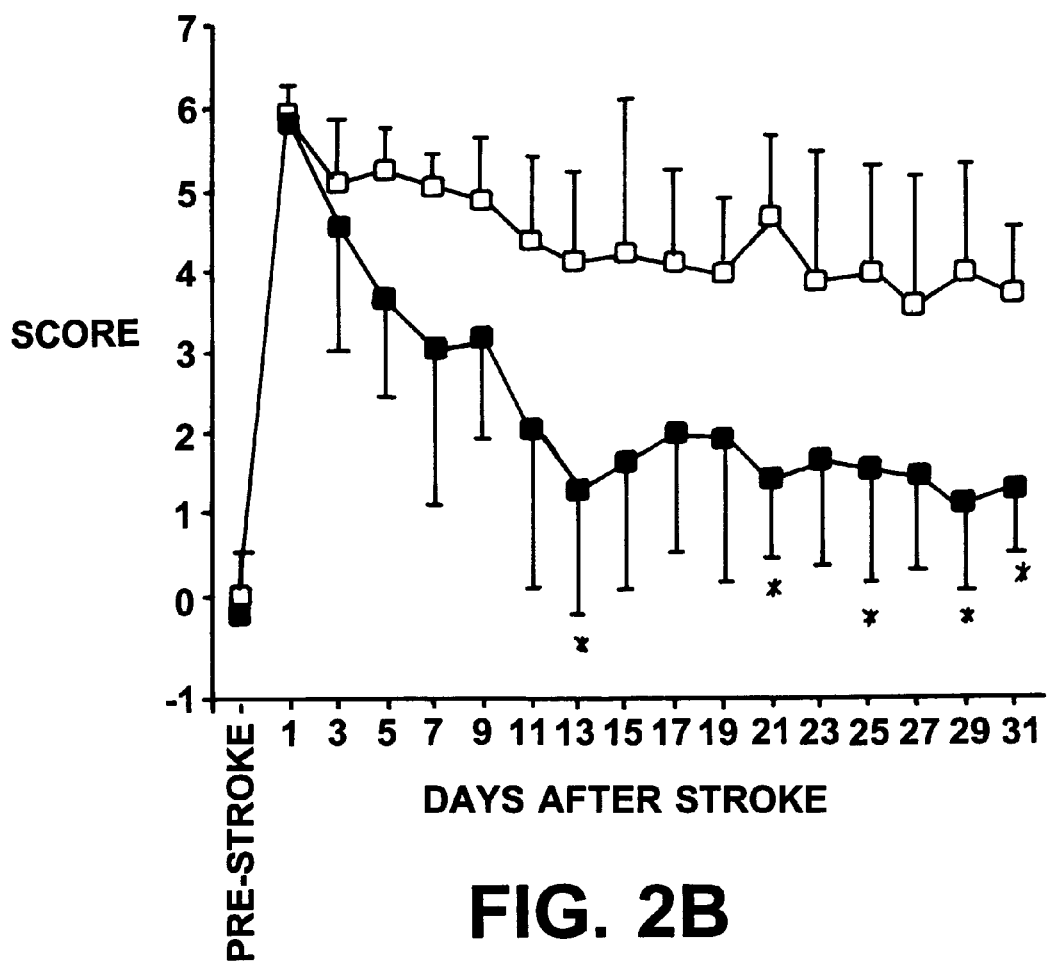
Figure 3A:
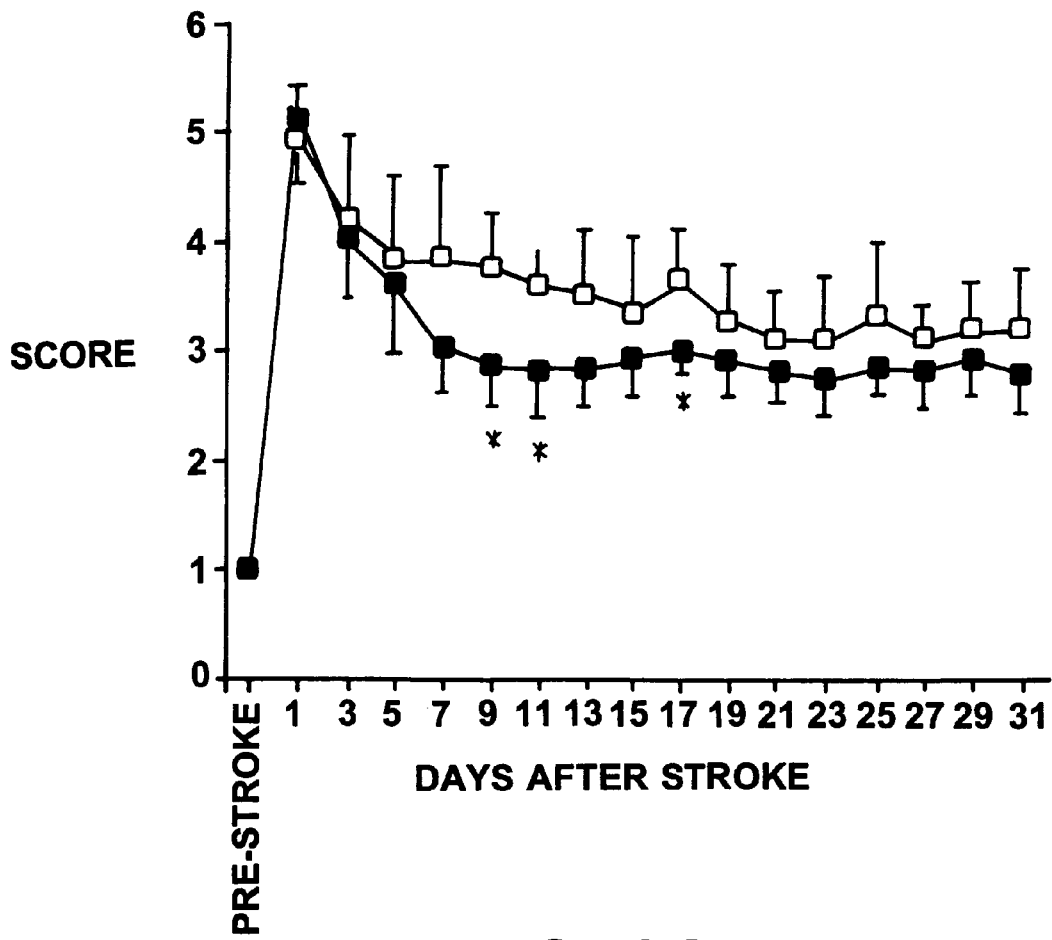
FIGS. 3A–3B are a pair of graphs depicting balance beam (3A) and postural reflex (3B) scores in bFGF treated animals (3 µg/kg/injection; total bFGF delivered=8 µg/animal; N=9 animals; closed squares) and vehicle-treated animals (N=8 animals, open squares). Data are means±SD. ANOVA (beam balance): treatment: $F(1)=7.5$, $p=0.02$. ANOVA (postural reflex): treatment: $F(1)=7.2$, $p=0.02$. *=values in bFGF-treated animals different from corresponding values in vehicle-treated animals by two-tailed unpaired t-tests with Bonferroni correction ($p<0.05$).
Figure 3B:
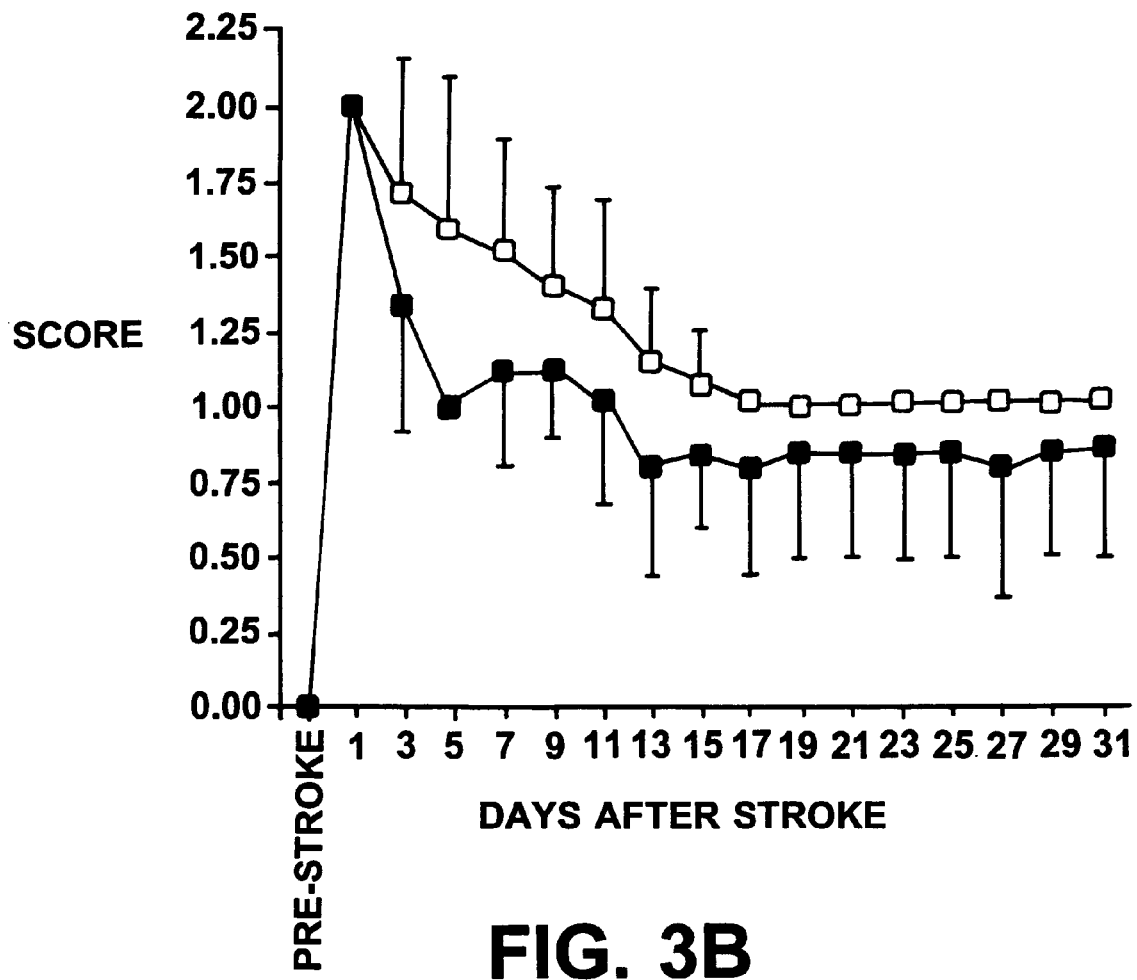

To develop a method for treating a patient following brain and/or spinal cord injury, the polypeptide growth factor basic FGF (bFGF) was administered to animals following occlusion of the middle cerebral artery (MCA). Occlusion of the MCA is a well accepted model of a focal ischemic episode and is thought to mimic the events that occur in humans following a stroke. Animals that were treated with bFGF, beginning 24 hours after occlusion of the MCA, performed significantly better than untreated animals in a variety of functional/behavioral tests.

The means by which a polypeptide growth factor can be administered to a patient who has suffered an ischemic attack within the central nervous system are first described and are followed by particular examples in which bFGF was administered either intracisternally or intravenously and shown to enhance recovery from surgically induced focal brain ischemia.

Polypeptide growth factors can be administered to a patient at therapeutically effective doses as follows. A therapeutically effective dose refers to a dose that is sufficient to result in functional recovery, beyond that which would be expected without administration of the polypeptide.

Effective Dose

Toxicity and therapeutic efficacy of a given polypeptide growth factor can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}$: $ED_{50}$. Polypeptides that exhibit large therapeutic indices are preferred. While polypeptide growth factors that exhibit toxic side effects can be used, care should be taken to design a delivery system that targets such compounds to the site of affected tissue in order to minimize potential damage to unaffected cells and, thereby, reduce side effects.

The data obtained from cell culture assays and animal studies, notably the studies of rats described below, can be used in formulating a range of dosage for use in humans. The dosage of such polypeptides lies preferably within a range of circulating concentrations that include the $ED_{50}$ with little or no toxicity. The dosage can vary within this range depending upon the dosage form employed and the route of administration utilized. For any polypeptide used in the method of the invention, the therapeutically effective dose can be estimated initially from the studies of surgically induced ischemia in the mammalian brain that are described below.

A dose can be formulated in animal models to achieve a circulating plasma concentration range that includes the $IC_{50}$ (that is, the concentration of the test polypeptide which achieves a half-maximal induction of recovery) as determined in the in vivo studies described below. Such information can be used to more accurately determine useful doses in humans. Levels in plasma can be measured, for example, by radioimmunoassay (RIA).

Formulations and Use

Pharmaceutical compositions for use in accordance with the present invention can be formulated in a conventional manner using one or more physiologically acceptable carriers or excipients.

Thus, the polypeptide growth factors can be formulated for administration by inhalation or insufflation (either through the mouth or the nose) or oral, buccal, parenteral, or rectal administration.

For oral administration, the pharmaceutical compositions can take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations can also contain buffer salts, flavoring, coloring, and sweetening agents as appropriate.

Preparations for oral administration can be suitably formulated to give controlled release of the active compound.

For buccal administration the compositions can take the form of tablets or lozenges formulated in a conventional manner.

The polypeptide growth factors can be formulated for parenteral administration by injection, for example, by bolus injection or continuous infusion. Formulations for injection can be presented in unit dosage form, for example, in ampules or in multi-dose containers, with an added preservative. The compositions can take such forms as suspensions, solutions, or emulsions in oily or aqueous vehicles, and can contain formulatory agents such as suspending, stabilizing, and/or dispersing agents. Alternatively, the active ingredient can be in powder form for constitution with a suitable vehicle, for example, sterile pyrogen-free water, before use.

The polypeptide growth factors can also be formulated in rectal compositions such as suppositories or retention enemas, for example, containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The polypeptide growth factors can, if desired, be presented in a pack or dispenser device which can contain one or more unit dosage forms containing the active ingredient. The pack can, for example, comprise metal or plastic foil, such as a blister pack. The pack or dispenser device can be accompanied by instructions for administration.

The therapeutic polypeptide growth factors of the invention can also contain a carrier or excipient, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. The nucleic acids, polypeptides, antibodies, or modulatory compounds of the invention can be administered by any standard route of administration. In addition to the routes of administration described above, the polypeptide growth factor can be administered intravenously, intraarterially, subcutaneously, intramuscularly, intracranially, intraorbitally, opthalmically, intraventricularly, intracapsularly, intraspinally, or intracisternally.

The polypeptide growth factor can be formulated in various ways, according to the corresponding route of administration. For example, liquid solutions can be made for ingestion or injection; gels or powders can be made for ingestion, inhalation, or topical application. Methods for making such formulations are well known and can be found in, for example, "Remington's Pharmaceutical Sciences" (A. Gennaro, Ed., Mack Publ., 1990). It is expected that the preferred route of administration will be intravenous. It is known that bFGF administered intravenously crosses the damaged blood brain barrier to enter ischemic brain tissue (Fisher et al., *J. Cereb. Blood Flow Metab.* 15:953–959, 1995; Huang et al., *Amer. J. Physiol.* in press).

It is well known in the medical arts that dosages for any one patient depend on many factors, including the general health, sex, weight, body surface area, and age of the patient, as well as the particular compound to be administered, the time and route of administration, and other drugs being administered concurrently. Determining the most appropriate dosage and route of administration is well within the abilities of a skilled physician.

Experimental Reagents and Procedures

Surgical Occlusion of the Middle Cerebral Artery

The animal model of ischemia used herein is the middle cerebral artery (MCA) occlusion model, which is a focal ischemia model (Kawamata et al., *J. Cereb. Blood Flow Metab.*, 16:542–547, 1996; Gotti et al., *Brain Res.* 522:290–307, 1990). The animals used in this study were male Sprague-Dawley rats weighing 250–300 grams (Charles River). For surgical procedures, the animals were anesthetized with 2% halothane in 70% $NO_2$/30% $O_2$. The tail artery was cannulated to enable blood gas and blood glucose monitoring. Body temperature was monitored using a rectal probe and was maintained at 37±0.5° C. with a heating pad. The proximal right middle cerebral artery (MCA) was occluded permanently using a modification of the method of Tamura et al. (*J. Cereb. Blood Flow Metab.* 1:53–60, 1981). Briefly, the proximal MCA was exposed transcranially without removing the zygomatic arch or transecting the facial nerve. The artery was then electrocoagulated using a bipolar microcoagulator from just proximal to the olfactory tract to the inferior cerebral vein, and was then transected (Bederson et al., *Stroke* 17:472–476, 1986). Rats were observed until they regained consciousness and were then returned to their home cages. Cefazolin sodium (40 mg/kg, i.p.), an antibiotic, was administered to all animals on the day before and just after stroke surgery in order to prevent infection.

Administration of Polypeptide Growth Factors

Recombinant human bFGF was obtained as a concentrated stock (2 mg/ml; Scios Nova Corp, Mountain View, Calif.), and stored at −80° C. In preparation for use, the stock solution was diluted with 0.9% saline containing 100 µg/ml bovine serum albumin (BSA; Boehringer-Mannheim, Cat. #711454), pH 7.4, to give a final bFGF concentration of 20 µg/ml. Control animals received solutions without bFGF but with all other components at the same final concentration.

Intracisternal Administration

For intracisternal injections, most animals were placed in one of two treatment groups: one group of animals received a dose of 3 µg/kg/injection ("high dose bFGF"), and a second group of animals received a dose of 1.5 µg/kg/injection ("low dose bFGF"). To administer the injection, the animals were anesthetized with halothane in 70% $NO_2$/30% $O_2$ and placed in a stereotaxic frame. The procedure for intracisternal injection of growth factor-containing solutions or vehicle-only solutions was identical.

The following is a description of intracisternal administration, as performed with "high dose" bFGF. Using aseptic technique, bFGF (N=9 animals at 3 µg/kg/injection; N=8 animals at 1.5 µg/kg/injection) or vehicle only (N=8 animals in the "high dose" bFGF study; N=6 animals in the "low dose" bFGF study) were introduced by percutaneous injection (50 µl/injection) into the cisterna magna using a Hamilton syringe fitted with a 26 gauge needle (Yamada et al.,*J. Cereb. Blood Flow Metab.* 11:472–478, 1991). Before each injection, 1–2 µl of cerebrospinal fluid (CSF) was drawn back through the Hamilton syringe to verify needle placement in the subarachnoid space. Preliminary studies demonstrated that a dye, 1% Evans blue, delivered in this fashion diffused freely through the basal cisterns and over the cerebral cortex within one hour of injection.

Intracisternal injections were made biweekly for four weeks, starting 24 hours after stroke (i.e., on post-stroke days 1, 4, 8, 11, 15, 18, 22, and 25). Animals were randomly assigned to either of the bFGF treatment groups, or to the vehicle treatment group.

A third group of animals received only two intracisternal injections of bFGF, at 0.5 µg/injection on the first and second days after stroke. Since the average weight of a rat is 300–400 grams, an equivalent dosage per weight, would be 1.5 µg/kg/injection. These injections were administered as described above. Control animals were matched to this treatment group as well, and received solutions without bFGF but with all other components at the same final concentration on the first and second days after stroke.

Intravenous Administration bFGF was prepared as described above (i.e., by dissolving in 0.9% saline with 100 µg/ml BSA) so that the final concentration was 30 µg/ml. The bFGF was then administered to rats intravenously at a rate of 50 µg/kg/hour for three hours. Administration occurred one day after MCA occlusion. Control animals were treated with an intravenous infusion that lacked bFGF, but otherwise contained the same constituents that were in the infusion received by the bFGF-treated animals.

Functional/Behavioral Testing

To accustom the animals to handling, which would be necessary for behavioral/functional testing, they were handled for three days before surgery, for 10 minutes each day. Following surgery, they were housed in individual cages.

Four functional/behavioral tests were used to assess sensorimotor and reflex function after infarction. The full details of these tests have been described elsewhere (Bederson et al., *Stroke* 17:472–476, 1986; DeRyck et al., *Brain Res.* 573:44–60, 1992; Markgraf et al., *Brain Res.* 575:238–246, 1992; Alexis et al., *Stroke* 26:2338–2346, 1995).

The Forelimb Placing Test

Briefly, the forelimb placing test is comprised of three subtests. Separate scores are obtained for each forelimb. For the visual placing subtest, the animal is held upright by the researcher and brought close to a table top. Normal placing of the limb on the table is scored as "0," delayed placing (<2 sec) is scored as "1," and no or very delayed placing (>2 sec) is scored as "2." Separate scores are obtained first as the animal is brought forward and then again as the animal is brought sideways to the table (maximum score per limb=4; in each case higher numbers denote greater deficits). For the tactile placing subtest, the animal is held so that it cannot see the table top or touch it with its whiskers. The dorsal forepaw is touched lightly to the table top as the animal is first brought forward and then brought sideways to the table. Placing each time is scored as above (maximum score per limb=4). For the proprioceptive placing subtest, the animal is brought forward only and greater pressure is applied to the dorsal forepaw; placing is scored as above (maximum score per limb=2). These subscores are added to give the total forelimb placing score per limb (range=0–10).

The Hindlimb Placing Test

The hindlimb placing test is conducted in the same manner as the forelimb placing test but involves only tactile and proprioceptive subtests of the hindlimbs (maximal scores 4 and 2, respectively; total score range=0–6).

The Modified Balance Beam Test

The modified balance beam test examines vestibulomotor reflex activity as the animal balances on a long, narrow beam (30×1.3 cm) for 60 seconds. Ability to balance on the beam is scored as follows: 1=animal balances with all four paws on top of beam; 2=animal puts paws on side of beam or wavers on beam; 3=one or two limbs slip off beam; 4=three limbs slip off beam; 5=animal attempts to balance with paws on beam but falls off; 6=animal drapes over beam, then falls off; 7=animal falls off beam without an attempt to balance. Animals received three training trials before surgery: the score of the last of these was taken as the baseline score.

The Postural Reflex Test

The postural reflex test measures both reflex and sensorimotor function. Animals are first held by the tail suspended above the floor. Animals that reach symmetrically toward the floor with both forelimbs are scored "0." Animals showing abnormal postures (flexing of a limb, rotation of the body) are then placed on a plastic-backed sheet of paper. Those animals able to resist side-to-side movement with gentle lateral pressure are scored "1," while those unable to resist such movement are scored "2." All functional/behavioral tests were administered just before stroke surgery and then every other day from post-stroke day 1 to post-stroke day 31. At each session, animals were allowed to adapt to the testing room for 30 minutes before testing was begun.

Histological Analysis

On post-stroke day 31 (i.e. 31 days after MCA occlusion), animals were anesthetized deeply with pentobarbital and perfused transcardially with heparinized saline followed by 10% buffered formalin. Brains were removed, cut into three pieces, and stored in 10% buffered formalin before dehydration and embedding in paraffin. Coronal sections (5 $\mu$m) were cut on a sliding microtome, mounted onto glass slides, and stained with hematoxylin and eosin. The area of cerebral infarcts on each of seven slices (+4.7, +2.7, +0.7, −1.3, −3.3, −5.3, and −7.3 compared to bregma) was determined using a computer-interfaced imaging system (Bioquant, R&M Biometnix, Inc., Nashville, Tenn.). Total infarct area per slice was determined by the "indirect method" as [the area of the intact contralateral hemisphere]–[the area of the intact ipsilateral hemisphere] to correct for brain shrinkage during processing (Swanson et al., *J. Cereb. Blood Flow Metab.* 10:290–293, 1990). Infarct volume was then expressed as a percentage of the intact contralateral hemispheric volume. The volumes of infarction in cortex and striatum were also determined separately using these methods.

The experimenter performing intracisternal injections, behavioral testing, and histological analysis was blinded to the treatments assigned until all data had been collected. Data were expressed as means±SD or means±SEM and were analyzed by repeated measures analysis of variance (ANOVA) followed by appropriate unpaired two-tailed t-tests, with the Bonferroni correction for multiple comparisons.

Immunostaining for Growth Associated Protein-43

Growth Associated Protein-43 (GAP-43) is a phosphoprotein component of the neuronal membrane and growth cone that is selectively upregulated during new axonal growth in both the peripheral and central nervous systems (Skene, *Ann. Rev. Neurosci.* 12:127–156, 1989; Aigner et al., *Cell* 83:269–278, 1995; Woolf et al., *Neuroscience* 34:465–478, 1990; Benowitz et al., *Mol. Brain Res.* 8:17–23, 1990). GAP-43 has been used as a reliable marker of new axonal growth during brain development, and following brain injury or ischemia (Stroemer et al., *Stroke* 26:2135–2144, 1995; Benowitz et al. supra; Vaudano et al., *J. Neurosci.* 15:3594–3611, 1995). GAP-43 immunoreactivity (IR) was examined in animals with focal infarcts (produced by MCA occlusion as described above) that either received or did not receive intracisternal bFGF. Animals that received bFGF were given 0.5 $\mu$g/injection, beginning at 24 hours after the infarction. Injections continued biweekly for four weeks, or until the animals was sacrificed.

For histological analysis, animals were killed 3, 7, or 14 days post-stroke surgery (by MCA occlusion) by transcardial perfusion fixation with normal saline followed by 2% formaldehyde, 0.01 M sodium-m-periodate, and 0.075 M L-lysine monohydrochloride in 0.1 M sodium phosphate buffer (pH 7.4; PLP solution). Their brains were removed, post-fixed, and cut into 40 $\mu$m sections on a vibratome. The sections were cryoprotected.

Free-floating sections were successively incubated in 20% normal goat serum, a mouse monoclonal antibody to GAP-43 (1:500, clone 91E12, Boehringer-Mannheim, Indianapolis, Ind.), and biotinylated horse anti-mouse IgG adsorbed against rat IgG (45 $\mu$l/10 ml; Vector, Burlingame, Calif.). Sections were then mounted onto glass slides, air dried, immersed in gradient ethanol, and coverslipped. Brain sections from all animals at each time point (i.e., animals sacrificed 3, 7, or 14 days post-stroke surgery) were immunostained simultaneously. Control sections were processed without primary antibody and showed no specific staining.

Following immunostaining, two standard coronal sections through the cerebral infarcts were examined; an "anterior" section at +0.2 mm compared to bregma and a "posterior" section at 02.8 mm compared to bregma. The relative changes in the intensity and extent of GAP-43 immunoreactivity (IR) were quantified using a computer-interfaced imagining system (Bioquant, Nashville, Tenn.) by two different methods. Adjacent brain sections, stained with hemotoxylin and eosin by standard procedures, were used to identify the extent of the infarct. The optical density (O.D.) of a region of reliably low GAP-43 IR (the corpus callosum) was considered the "background" value for each section.

Measurements were made in two ways. In one way, all brain regions showing an O.D. of at least 1.5 times the O.D. of the background were identified and highlighted (FIGS. 9A–9D and FIGS. 10A–10D). The area (in mm$^2$) of highlighted regions in the dorsolateral sensorimotor cortex was determined for each slice, and averaged among animals in each group. In the second way, specific regions of dorsolateral sensorimotor cortex were identified using a published standard rat brain atlas (Paxinos and Watson, "The Rat Brain in Stereotaxic Coordinates," Academic Press, San Diego, Calif.). On "anterior" brain sections, these included the medial peri-infarct cortex (51 mm from the infarct border) in the ipsilateral hemisphere, and frontal cortex areas 1 and 2 (FR 1,2) and forelimb area of cortex (FL) regions in both hemispheres (FIGS. 9A–9E). On "posterior" sections, these included the medial peri-infarct region in the ipsilateral hemisphere, as well as FR 1,2 and hindlimb area of cortex (HL) regions bilaterally (FIGS. 10A–10E). The O.D. was determined for each region on each section and normalized to background. For each method, data in sham or vehicle-treated and data in sham or bFGF-treated animals were not different, so these values were pooled in the analysis. Data in all groups were expressed as ratios compared to stroke/vehicle-treated animals.

Results

There was no Difference in Total Infarct Volume Between bFGF-Treated, or Vehicle-Treated Animals During stroke surgery, there were no differences in the levels of blood gases or glucose among animals that subsequently received bFGF or vehicle treatment. Among surviving animals, sacrifice at day 31 showed large infarcts in the right lateral cerebral cortex and underlying striatum in the territory of the MCA (FIG. 1). Brain regions severely damaged by infarcts included parietal cortex, areas 1 and 2 (Par1, Par2) and granular insular cortex (GI). Regions partially damaged by infarcts included frontal cortex, areas 1, 2, and 3 (FR1, FR2, FR3); agranular insular cortex (AI); temporal cortex, areas 1 and 3 (Tel1, Tel3); lateral occipital cortex, area 2 (Oc2L); the cortical forelimb area (FL), and the caudoputamen (cPu; Paxinos and Watson, 1986). The cortical hindlimb area (HL) was generally spared from infarcts.

There was no difference in total infarct volume between animals treated with 3 μg/kg/injection of bFGF ("high dose" bFGF) and vehicle-treated animals ($31.1 \pm 5.9$ vs. $30.0 \pm 5.3\%$ of intact contralateral hemispheric volume, N=9 vs. N=8, respectively, t=0.4, p=n.s.). Similarly, there was no difference in total infarct volume between animals treated with 1.5 μg/kg/injection of bFGF ("low dose" bFGF), or vehicle-treated animals. Moreover, there was no difference in cortical or striatal infarct volume among the growth factor-treated animals and the vehicle-treated animals, when these volumes were calculated separately.

Inspection of hematoxylin and eosin-stained sections showed no evidence of abnormal cell proliferation in the brains of bFGF-treated animals.

Animals Treated with bFGF Performed Better than Animals Treated with Vehicle in Functional Tests Following infarction, animals showed severe disturbances of sensorimotor and reflex function on all four behavioral tests. For the limb placing tests, deficits were confined to the contralateral (left) limbs. Animals showed partial recovery on all four behavioral tests during the first month after stroke (FIGS. 2A–2B and FIGS. 3A–3B). Moreover, bFGF-treated animals recovered more rapidly and to a greater degree than vehicle-treated rats. Improved recovery of surviving bFGF- vs. vehicle-treated animals was most pronounced for the forelimb and hindlimb placing tasks, and less pronounced, although still significant, for the beam balance and postural reflex tests. See FIGS. 2A–2B and FIGS. 3A–3B for the performance of animals in the four behavioral tests performed after receiving "high" doses of bFGF intracisternally, and FIGS. 5A–5B and FIGS. 6A–6B for the performance of animals in the four behavioral tests performed after receiving "low" doses of bFGF intracisternally. Enhanced recovery was seen on all subtests of the limb placing tests (visual, tactile, and proprioceptive) following bFGF treatment.

Figure 4:
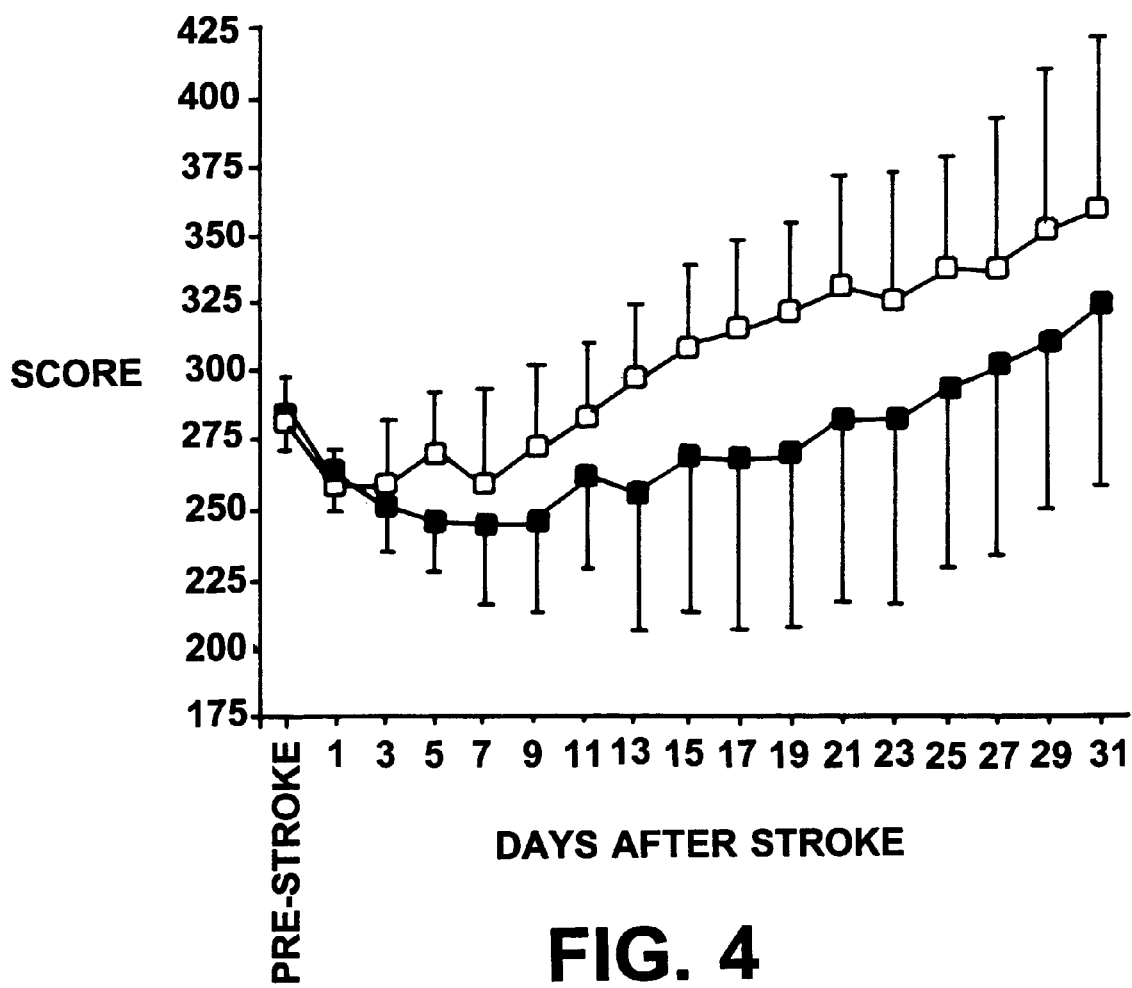
FIG. 4 is a graph depicting body-weight in bFGF-treated animals (3 µg/kg/injection; total bFGF delivered=8 µg/animal; N=9 animals; closed squares) and vehicle-treated animals (N=8 animals; open squares). Data are means±SD. ANOVA: treatment $F(1)=2.8$, $p=$n.s.
Figure 5A:
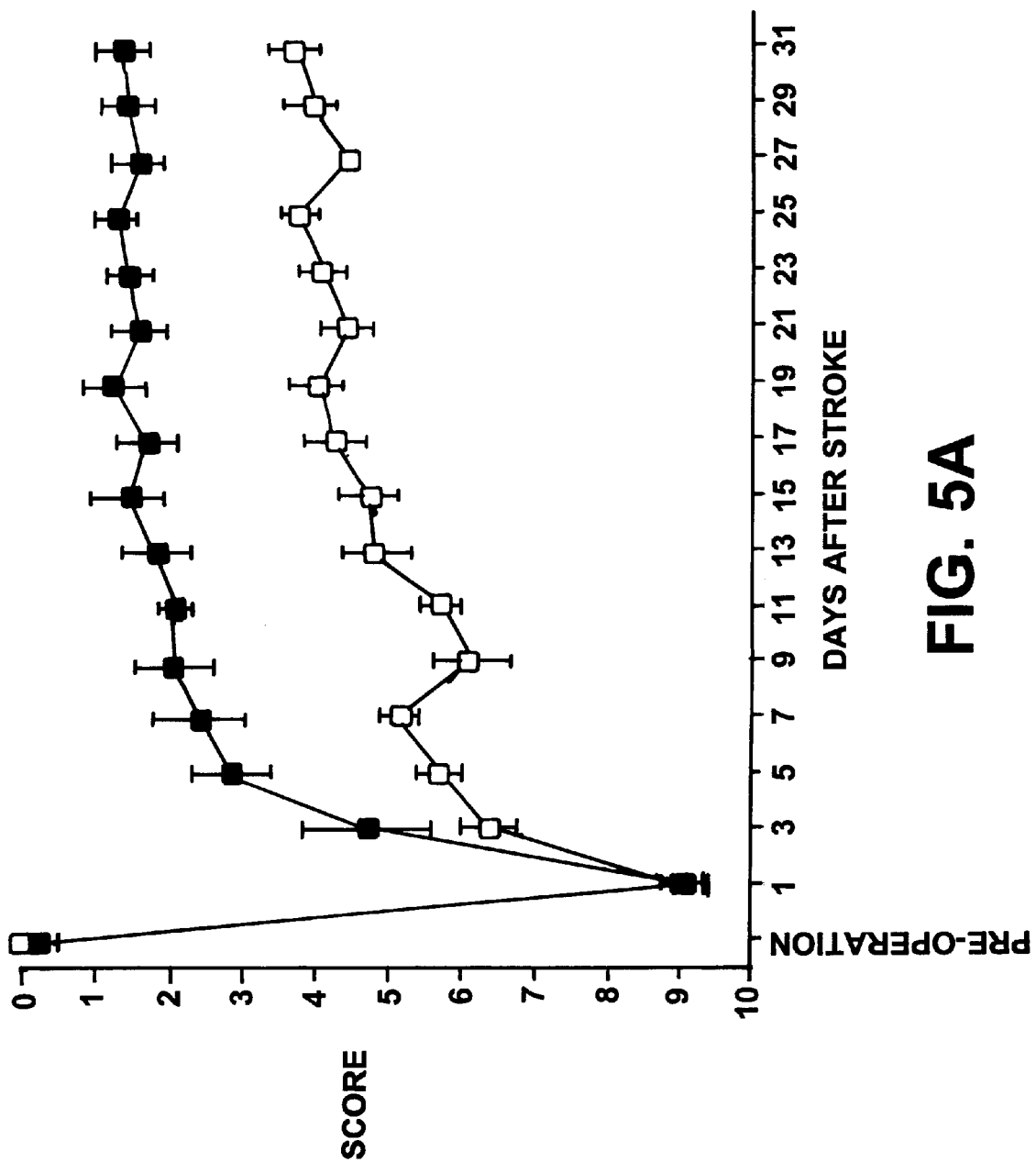
FIGS. 5A–5B are a pair of graphs depicting forelimb placing (5A) and hindlimb placing (5B) scores of affected (left) limbs of low dose (LD) bFGF-treated animals (1.5 µg/kg/injection; total bFGF delivered=4 µg/animal; N=8 animals; closed squares) and vehicle-treated animals (N=6 animals; open squares). Data are means±SEM. ANOVA (forelimb placing): treatment:$F(1)=32.65$, $p=0.0001$. ANOVA (hindlimb placing): treatment: $F(1)=34.58$, $p=0.0001$.
Figure 5B:
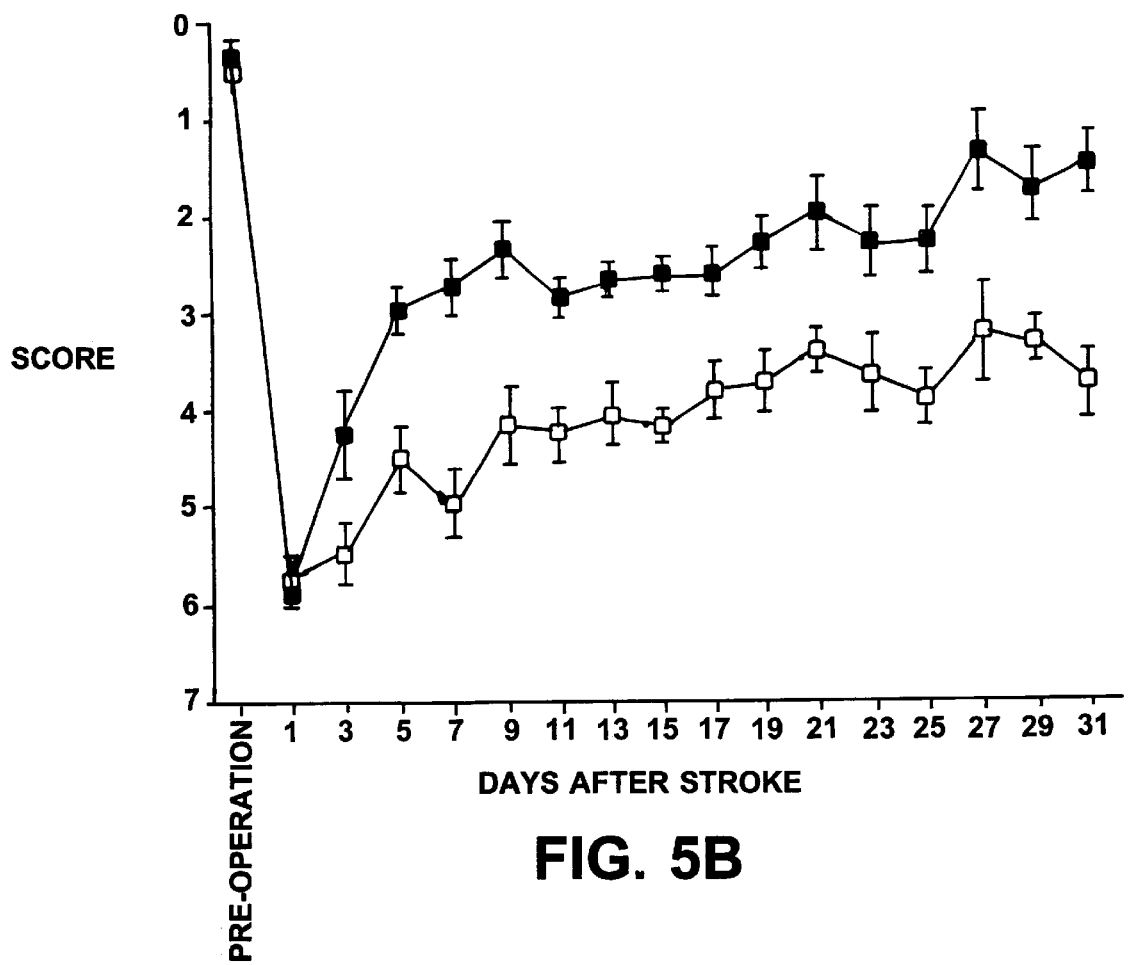
Figure 6A:
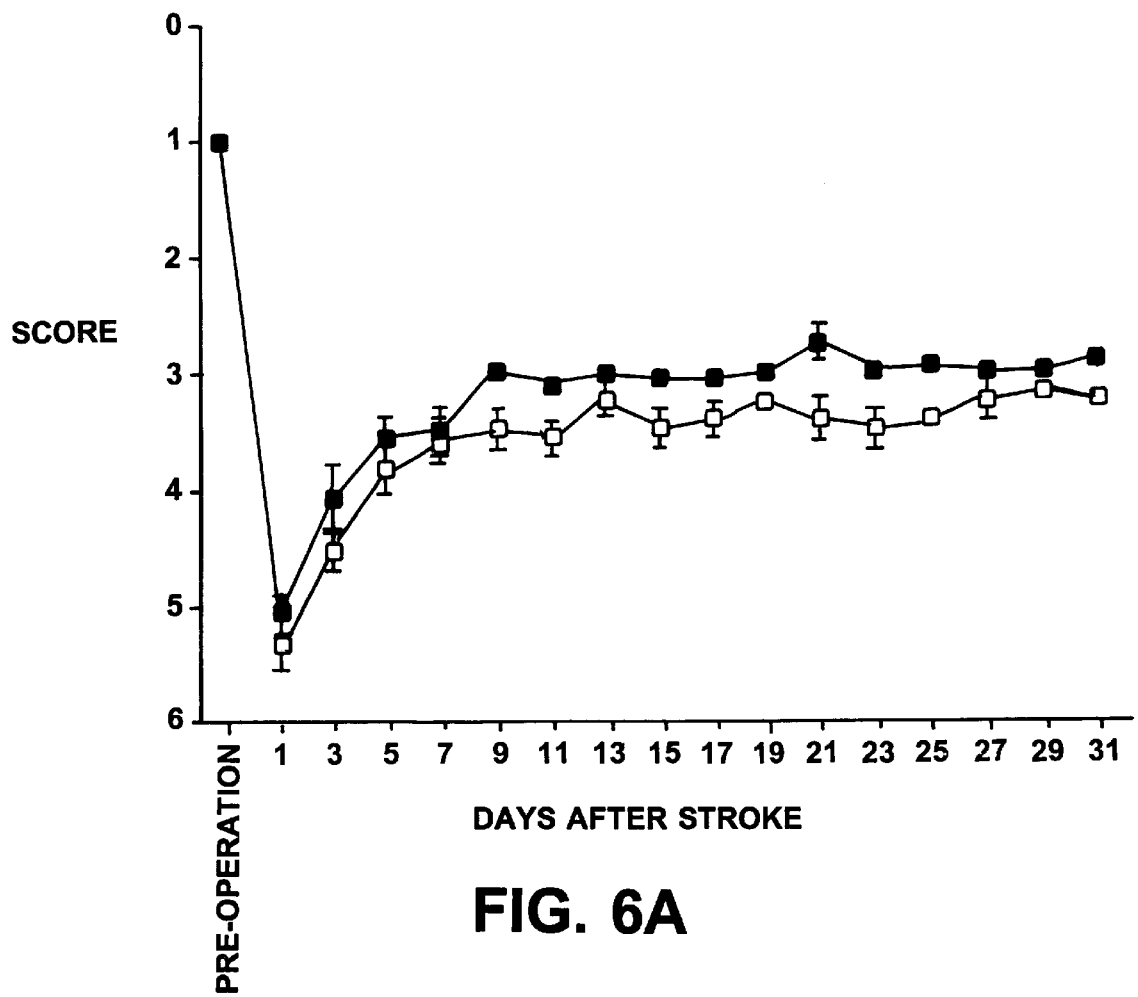
FIGS. 6A–6B are a pair of graphs depicting beam balance (6A) and postural reflex (6B) scores in low dose bFGF-treated animals (1.5 µg/kg/injection; total bFGF delivered=4 µg/animal; N=8 animals; closed squares) and vehicle-treated animals (N=6, open squares). Data are means±SEM. ANOVA (beam balance): treatment $F(1)=15.933$, $p=0.0018$. ANOVA (postural reflex): treatment: $F(1)=1.998$, $p=$n.s.
Figure 6B:
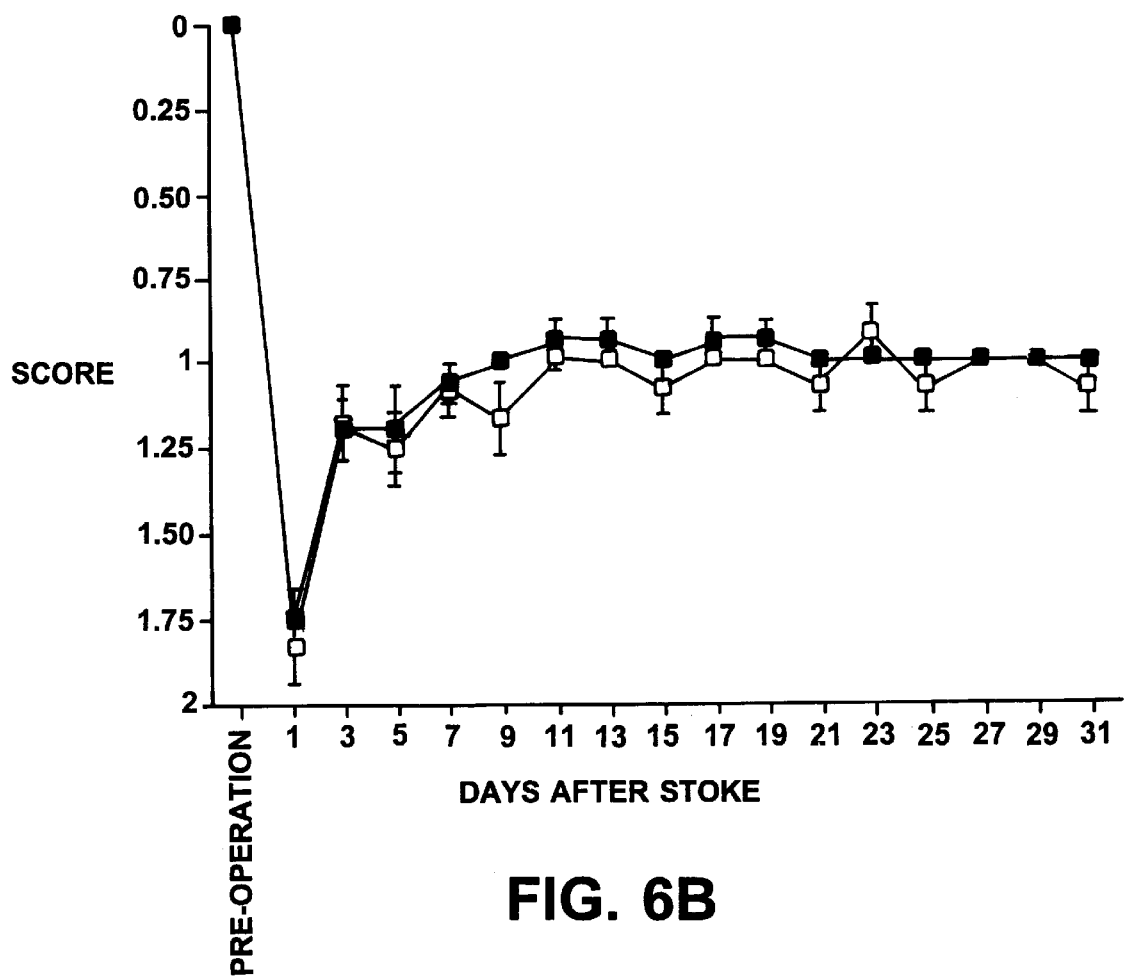

Five of the 14 animals that were treated with the higher dose of bFGF, i.e., with 3 μg/kg/injection, experienced severe progressive weight loss during the first month after stroke and died. The performance of these animals was comparable to that of surviving bFGF-treated animals until the time of their death at 7–23 days after stroke. The mean weight of animals that were treated with 3 μg/kg/injection of bFGF and that died was $165 \pm 11$ g on the day of death. The animals that were treated with this same dose, but survived, exhibited a small degree of initial weight loss followed by a gradual recovery of body weight after stroke (FIG. 4). Survival of bFGF-treated animals tended to recover body weight more slowly than vehicle-treated rats (FIG. 4). In contrast, animals treated with a lower dose of bFGF, i.e., 1.5 μg/kg/injection were no different in weight than animals that were treated with vehicle only. The animals that received a lower dose of bFGF did not experience the weight loss incurred at the higher dosage; their weight was the same as that of the vehicle-only treated animals (FIG. 7), and they performed better than vehicle-treated animals in both forelimb and hindlimb placing tests (FIGS. 5A–5B).

Figure 8A:
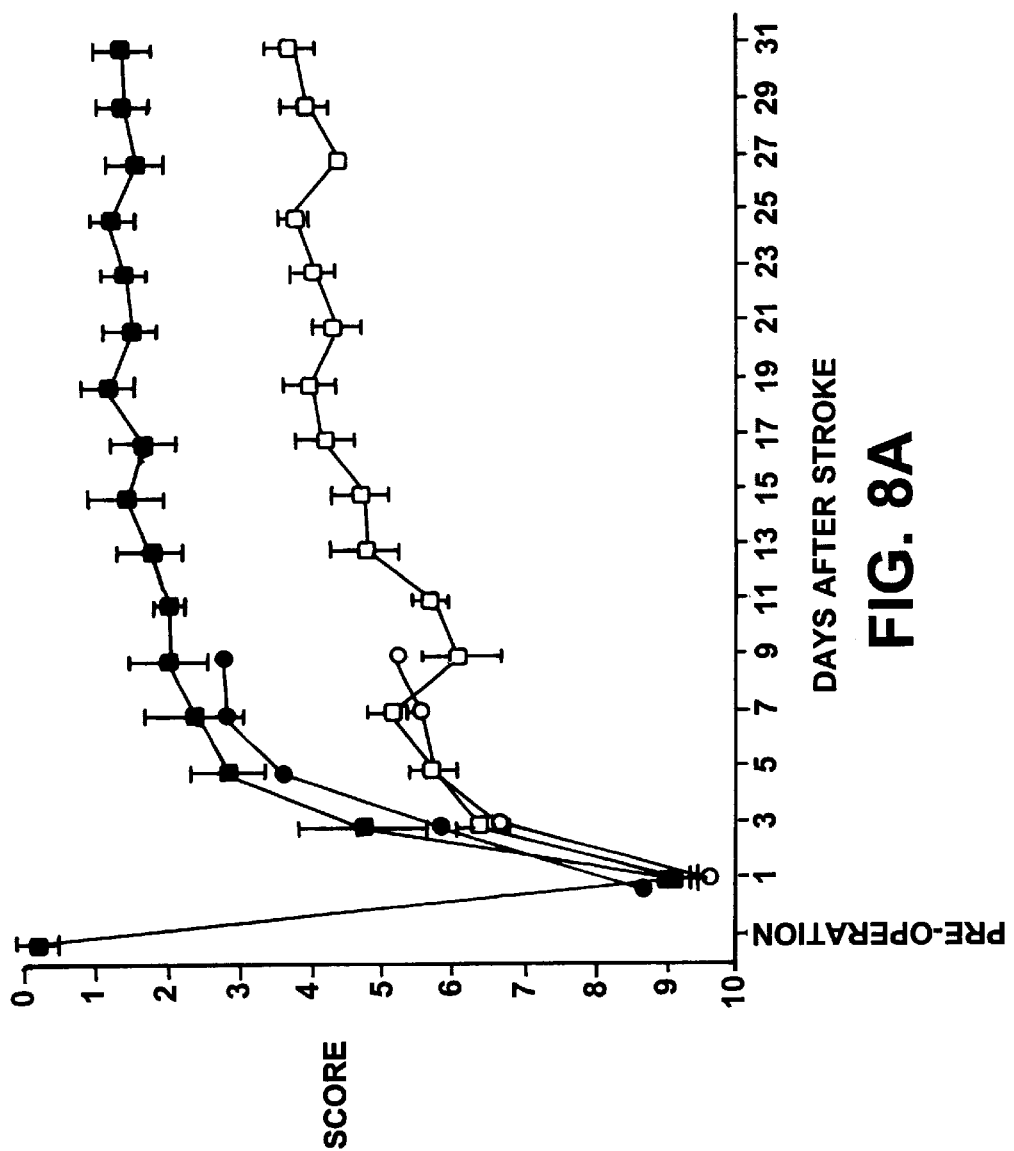
FIGS. 8A–8B are a pair of graphs depicting forelimb placing (8A) and hindlimb placing (8B) scores of affected (left) limbs of animals treated by intravenous injection of bFGF (at 50 µg/kg/hour for 3 hours; see closed circles) or of animals treated by intravenous injection of vehicle alone (see open circles). These data are presented along with that obtained from animals those received intracisternal injections of bFGF biweekly (at 0.5 µg/kg/injection, i.e., low dose bFGF-treated animals) to show that recovery is comparable.
Figure 8B:
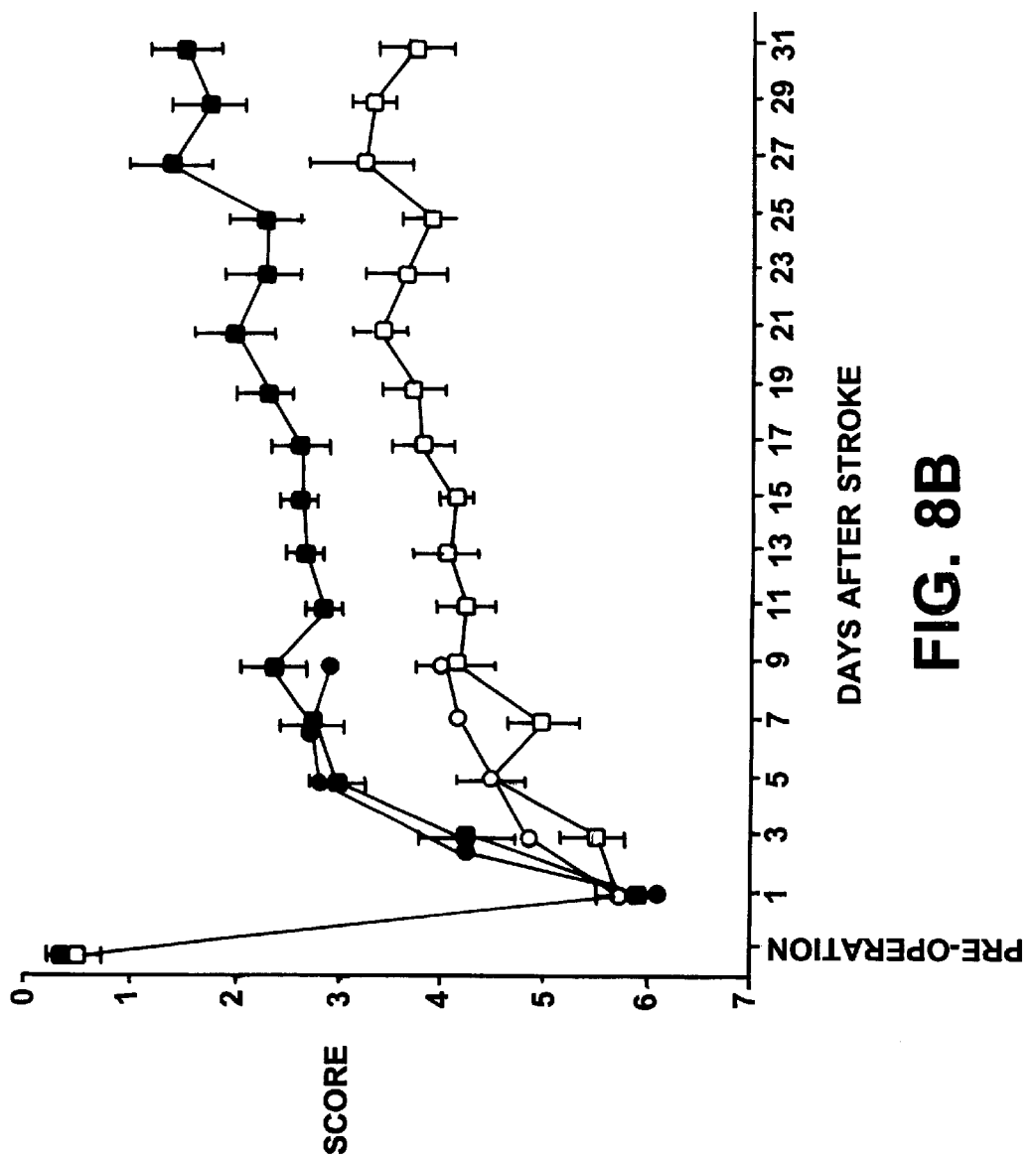

The recovery of animals that were given only 2 injections of bFGF (i.e. 0.5 μg/injection of bFGF on the first and second days after stroke) was comparable to the recovery of animals that were given 8 injections of bFGF (i.e., biweekly injections of either "high" or "low" dose bFGF for one month). For example, by 30 days after the stroke, the average score in the forelimb placing test of animals given 8 biweekly intracisternal injections (of either 3 or 1.5 μg/kg/injection) of bFGF was approximately "2," as was the average score of the animals given intracisternal injections (of 1.5 μg/kg/injection) of bFGF on only the first and second days after the stroke. In contrast, the average score in this same test for all nonbFGF treated animals was approximately "5."

bFGF also enhanced recovery (following MCA occlusion) when administered intravenously. As shown in FIGS. 8A–8B, forelimb placing (FIG. 8A) and hindlimb placing (FIG. 8B) by animals given bFGF intravenously (see the closed circles) was equivalent to that of animals that were given bFGF intracisternally (at 0.5 μg/kg/injection for 4 weeks). The animals that served as controls for the intravenously injected group recovered to the same extent as the control animals for the intracisternally injected group (see the open circles on FIGS. 8A–8B). Furthermore, the body weight of animals that were treated intravenously with bFGF were no different than the weight of animals given bFGF intracisternally.

Based on these results, both intracisternal and intravenous administration of bFGF, starting at least one day after ischemia, enhance behavioral recovery following focal cerebral infarction. Improved behavioral recovery in the rat model of ischemia used herein was seen without a change in infarct volume in bFGF-treated compared to vehicle-treated animals. The bFGF was given starting at one day after ischemia, beyond the apparent "therapeutic window" during which bFGF can reduce infarct size. The current findings represent the first demonstration that an exogenously administered neurotrophic growth factor can enhance behavioral recovery without a reduction in infarct size in an animal model of stroke.

Enhancement of recovery by bFGF was most pronounced on tests of sensorimotor function of the affected limbs and less pronounced on tests of reflex and postural function. Our infarcts did not completely damage forelimb and hindlimb cortical areas, which is compatible with recovery on limb placing tests following focal infarction in the MCA territory. Treatment with bFGF enhanced both the rate and degree of behavioral recovery during the first month after infarction.

GAP-43 Immunoreactivity is Selectively Increased in the Intact Sensorimotor Cortex Contralateral to Cerebral Infarcts Following bFGF Treatment Possible mechanisms by which bFGF enhances recovery can include: (1) protection against retrograde cell death and/or (2) acceleration of new neuronal sprouting and synapse formation. It is possible that distant neurons in thalamus and elsewhere, spared by bFGF treatment, might establish new functional connections, thereby enhancing recovery. While not wishing to be bound to a particular underlying mechanism of action, examination of GAP-43 expression indicates that new growth of axonal processes, and possibly of dendritic processes, is likely to play an important role in functional recovery from ischemic injury.

At all time points examined (see above), the pattern of GAP-43 immunoreactivity in sham-operated animals receiving either bFGF or vehicle was similar to that described previously for the intact, mature rat brain (Benowitz et al., *J. Neurosci.* 8:339–352, 1988). Specifically, GAP-43 immunoreactivity was relatively high in the ventrolateral cerebral cortex and striatum, hypothalamus, parts of the thalamus, amygdala, and hippocampal formation. GAP-43 immunoreactivity was relatively low in the dorsolateral sensorimotor cortex, except for parts of FR 1,2, cortex in "anterior" brain sections and HL cortex in "posterior" sections.

Following stroke (induced by MCA occlusion), increased GAP-43 immunoreactivity was found in peri-infarct cortex in the ipsilateral hemisphere, peaking at three days after ischemia, consistent with previous reports (Stroemer, supra). There were no differences in GAP-43 immunoreactivity in the ipsilateral peri-infarct cortex between stroke/vehicle-treated and stroke/bFGF-treated animals. No differences were found in the contralateral hemisphere of stroke/vehicle-treated compared to sham/vehicle-treated or sham/bFGF-treated animals (FIGS. 9A–9E and FIGS. 10A–10E). However, in stroke/bFGF-treated animals, a selective increase in GAP-43 immunoreactivity was found within the contralateral sensorimotor cortex. Specifically, regions of high GAP-43 immunoreactivity were larger, spreading ventrally to involve the entire FR 1,2 cortex and part of FL cortex in "anterior" brain sections (FIGS. 9A–9E), and to involve Par1 cortex in "posterior" brain sections (FIGS. 10A–10E).

Side Effects

Only treatment with the higher of two intracisternal doses of bFGF produced side effects. When the dosage was reduced from 3.0 µg/kg/injection to 1.5 µg/kg/injection, functional/behavioral recovery was enhanced but animals did not experience weight loss, and no animals died. Similarly, animals that received bFGF intravenously did not experience weight loss, and no animals died. It is unlikely that the improved behavioral scores we observed at the higher dosage were simply an artifact of lower body weight because all of the behavioral tests used, except the beam balance test, were done with the researcher supporting the animal. Of additional note is that, in spite of known mitogenic effects of bFGF on glial and endothelial cells, there was no gross evidence of abnormal cell proliferation in brains of bFGF-treated animals.

What is claimed is:

1. A method for improving a sensorimotor deficit in a human patient who has suffered an injury to the central nervous system, the method comprising administering to the human patient a polypeptide growth factor in sufficient dosage to improve a sensorimotor deficit caused by the injury, the administration beginning more than twelve hours after the onset of the injury.

2. The method of claim 1, wherein said injury comprises an ischemic episode.

3. The method of claim 2, wherein said ischemic episode is global cerebral ischemia.

4. The method of claim 2, wherein said ischemic episode is focal cerebral ischemia.

5. The method of claim 2, wherein said ischemic episode is caused by hypertension, hypertensive cerebral vascular disease, rupture of an aneurysm, an embolus, a thrombus, an angioma, blood dyscrasias, cardiac failure, systemic hypotension, cardiac arrest, cardiogenic shock, septic shock, spinal cord trauma, head trauma, seizure, bleeding from a tumor, or other blood loss.

6. The method of claim 1, wherein said injury is a traumatic injury.

7. The method of claim 1, wherein said polypeptide growth factor is a fibroblast growth factor (FGF).

8. The method of claim 7, wherein said fibroblast growth factor is basic FGF (bFGF), acidic FGF (aFGF), the hst/Kfgf gene product, FGF-5, int-2, or active fragments thereof.

9. The method of claim 1, wherein said polypeptide growth factor is a neurotrophin.

10. The method of claim 9, wherein said neurotrophin is nerve growth factor (NGF), brain-derived neurotrophic factor (BDNF), neurotrophin 3 (NT3), or neurotrophin 4/5 (NT4/5), or active fragments thereof.

11. The method of claim 1, wherein said polypeptide growth factor is ciliary neurotrophic growth factor (CNTF), leukemia inhibitory factor (LIF), oncostatin M, or an interleukin.

12. The method of claim 1, wherein administration of the polypeptide growth factor begins more than 24 hours after an injury to the central nervous system.

13. The method of claim 1, wherein administration of the polypeptide growth factor begins more than 48 hours after an injury to the central nervous system.

14. The method of claim 1, wherein the administration comprises intravenous administration of 10 to 1,000 µg/kg of a polypeptide growth factor.

15. The method of claim 1, wherein administration of the polypeptide growth factor comprises intracerebral administration.

16. The method of claim 15, wherein said intracerebral administration is intracisternal.

17. The method of claim 16, wherein said intracisternal administration comprises administration of a single injection of approximately 0.1 to 100 µg/kg/injection.

18. The method of claim 17, wherein administration begins approximately 24 hours after the injury to the central nervous system.

19. The method of claim 16, wherein said intracisternal administration comprises administration of a series of injections of approximately 1.5 to 3.0 µg/kg/injection.

20. The method of claim 19, wherein said administration occurs biweekly.

21. The method of claim 19, wherein administration begins approximately 24 hours after the injury to the central nervous system.

22. The method of claim 1, wherein administration of the polypeptide growth factor comprises intrathecal administration.

23. A method for treating a patient who has suffered an injury to the central nervous system, the method comprising intravenously administering to the patient a polypeptide growth factor, the administration beginning more than twelve hours after the onset of the injury.

24. The method of claim 23, wherein the polypeptide growth factor is basic fibroblast growth factor.

25. The method of claim 1, wherein the polypeptide growth factor is basic fibrobalst growth factor.

26. A method for treating a patient who has suffered an injury to the central nervous system, the method comprising administering to the patient a total of at least 1.0 µg of a polypeptide growth factor, the administration commencing more than forty-eight hours after the onset of the injury.

* * * * *

UNITED STATES PATENT AND TRADEMARK OFFICE
CERTIFICATE OF CORRECTION

PATENT NO.    : 6,214,796 B1
DATED         : April 10, 2001
INVENTOR(S)   : Seth P. Finklestein It is certified that error appears in the above-identified patent and that said Letters Patent is hereby corrected as shown below:

<u>Title page,</u>
In the citation for: Rosenberg et al., delete "Continum" should be deleted and replace it with -- Continuum --.

<u>Column 6,</u>
Line 4, delete "that" and replace it with -- those --.
Line 5, delete "those" and replace it with -- that --.

<u>Column 10,</u>
Line 30, delete "." after "occurred".

<u>Column 12,</u>
Line 53, delete "(51mm" and replace it with -- ($\leq 1$ mm --.

Signed and Sealed this

Eighth Day of January, 2002

Attest:

JAMES E. ROGAN
*Attesting Officer*     *Director of the United States Patent and Trademark Office*